United States Patent

Meier et al.

(10) Patent No.: US 6,365,653 B1
(45) Date of Patent: Apr. 2, 2002

(54) THIODIPROPIONIC ACID BISAMIDES AS STABILIZERS FOR NONBLACK ELASTOMERS

(75) Inventors: Hans-Rudolf Meier, Marly; Gerrit Knobloch, Magden, both of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/698,971

(22) Filed: Oct. 27, 2000

Related U.S. Application Data

(63) Continuation of application No. 09/188,591, filed on Nov. 9, 1998, now abandoned.

(30) Foreign Application Priority Data

Nov. 14, 1997 (CH) .............................................. 2641/97

(51) Int. Cl.⁷ .......................... C08K 5/41; C07C 317/36
(52) U.S. Cl. ........................ 524/155; 524/171; 564/154
(58) Field of Search ................................. 524/155, 171, 524/214, 217, 225; 564/154

(56) References Cited

U.S. PATENT DOCUMENTS

| | | | |
|---|---|---|---|
| 2,981,717 A | 4/1961 | Boultbee | 524/290 |
| 3,446,807 A | 5/1969 | Wagner | 560/150 |
| 3,479,408 A | 11/1969 | Perrino et al. | 560/150 |
| 3,494,947 A | 2/1970 | Schutz et al. | 560/150 |
| 3,975,414 A | 8/1976 | Kline | 260/42.47 |
| 4,216,160 A * | 8/1980 | Dorn et al. | 564/154 |
| 4,633,016 A | 12/1986 | Buysch et al. | 564/154 |
| 4,754,066 A | 6/1988 | Buysch et al. | 564/221 |
| 4,929,659 A | 5/1990 | Ravichandran | 524/155 |
| 5,641,820 A | 6/1997 | Wideman et al. | 524/225 |

OTHER PUBLICATIONS

Russel A Mazzeo et al., "Tire Technology International" 1994, pp. 36–46.

Donald E. Miller et al., Rubber World, 200 (5), pp. 13–23 (1989).

H. Schmid et al., Helvetica Chimica Acta 34, pp. 894–897 (1951).

Hans–Georg Elias, "An introduction to Polymer Science", Chapter 12, "Elastomers", pp. 388–393, 1997, VCH Verlagsgesellschaft mgH, Weinheim, Germany.

Ullmann's Encyclopedia of Industrial Chemistry, Fifth, Completely Revised Edition, vol. A 23, pp. 221–440 (1993).

J. Shelton, "Stabilization Fundamentals in Thermal Antioxidation of Polymers", pp. 217–225, *Stabilization and Degradation of Polymers*, American Chemical Society, (1978).

* cited by examiner

*Primary Examiner*—Veronica P. Hoke
(74) *Attorney, Agent, or Firm*—Kevin T. Mansfield; Tyler A. Stevenson

(57) ABSTRACT

Nonblack elastomers, which have excellent stability against oxidative, light- or ozone-induced degradation, comprise as stabilizers at least one compound of formula I

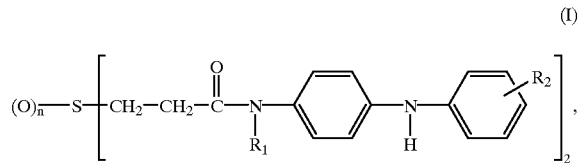

wherein $R_1$ is hydrogen, $C_1$–$C_{12}$alkyl, cyclohexyl, phenyl or benzyl, $R_2$ is hydrogen or $C_1$–$C_4$alkyl, and n is the number 0, 1 or 2. The compounds of formula I are excellently suitable as colour-stable and nonstaining stabilizers and antiozonants for protecting nonblack elastomers against oxidative, thermal, light- or ozone-induced degradation.

12 Claims, No Drawings

THIODIPROPIONIC ACID BISAMIDES AS STABILIZERS FOR NONBLACK ELASTOMERS

This is a continuation of application Ser. No. 09/188,591, filed Nov. 9, 1998 now abandoned.

The present invention relates to compositions comprising a nonblack elastomer, which is subject to oxidative, thermal, light- or ozone-induced degradation, and as stabiliser at least one thiodipropionic acid bisamide, as well as to the use thereof as colour-stable and non-staining stabilisers and antiozonants for protecting nonblack elastomers against oxidative, thermal, light- or ozone-induced degradation, as well as to a process for stabilising and reducing the discoloration of nonblack elastomers, which comprises incorporating in, or applying to, said elastomers at least one thiodipropionic acid bisamide.

Like all polymers, rubber articles (vulcanisates) are subject to oxidative, thermal or light-induced degradation. A particularly damaging factor for diene rubber vulcanisates is ozone. Ozone attacks the carbon carbon double bonds, many of which are still present in the rubber (vulcanisate) and, via the mechanism known as ozonolysis, results in damages which show as typical surface cracking and as failure of the rubber article. These damages are particularly serious in the case of rubber articles under dynamic stress.

To prevent ozone damages, age protectors from the class of the paraphenylene diamines [see Russel A. Mazzeo et al., Tire technology International 1994, pages 36–46; or Donald E. Miller et al., Rubber World, 200 (5), 13–23 (1989] are usually added to the vulcanisates. These compounds have an excellent protective effect especially under dynamic conditions, but develop strong discoloration and, owing to the high migration rates, exhibit intense contact staining, i.e. the colour transfers to other substrates/articles on direct contact. Therefore, the stabilisers used in the prior art can be used neither for carbon black-free or nonblack rubber articles nor for carbon black-containing (black) rubber articles which are to be used in direct contact with nonblack articles.

There thus continues to be a demand for colour-stable stabilisers protecting nonblack rubber articles against ozone. There is also still a demand for stabilisers which, although they may possess inherent colour, are not able to transfer that colour to other articles owing to, for example, chemical linkage to the rubber chain.

It has now been found that specific thiodipropionic acid bisamides are particularly suitable as stabilisers for nonblack elastomers which are susceptible to oxidative, thermal, light- or ozone-induced degradation.

Accordingly, this invention relates to compositions, which comprise
a) a nonblack elastomer subject to oxidative, thermal, light- or ozone-induced degradation, and
b) at least one compound of formula I

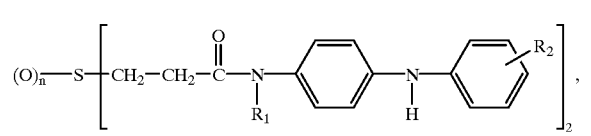

(I)

wherein
R$_1$ is hydrogen, C$_1$–C$_{12}$alkyl, cyclohexyl, phenyl or benzyl,
R$_2$ is hydrogen or C$_1$–C$_4$alkyl, and
n is the number 0, 1 or 2.

Alkyl containing up to 12 carbon atoms is a branched or unbranched radical, such as methyl, ethyl, propyl, isopropyl, n-butyl, sec-butyl, isobutyl, tert-butyl, 1,1-dimethyl-1-propyl, 2-ethyl-butyl, n-pentyl, isopentyl, 2-pentyl, 2-hexyl, 2-heptyl, 2-octyl, n-octyl, nonyl, decyl, undecyl or dodecyl. A preferred meaning of RI is, for example, C$_3$–C$_{12}$alkyl, in particular C$_3$–C$_8$ alkyl, e.g. isopropyl. A particularly preferred meaning of R$_2$ is, for example, methyl and ethyl.

Preferred compositions are those comprising as component (b) at least one compound of formula I, wherein
R$_1$ is hydrogen or C$_3$–C$_8$ alkyl,
R$_2$ is hydrogen or methyl, and
n is the number 0 or 1.

Particularly preferred compositions are those comprising as component (b) at least one compound of formula I, wherein
R$_1$ is hydrogen or C$_3$–C$_8$alkyl,
R$_2$ is hydrogen, and
n is the number 0 or 1.

Some of the compounds of formula I are known from the literature and they can be reacted, for example, starting from the known compounds of formula II

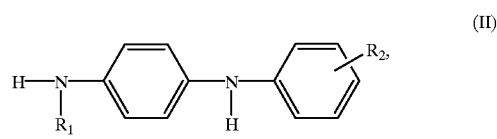

(II)

with half an equivalent of thio-3,3-bispropionic acid dichloride [preparation see H. Schmid et al., Helvetica Chimica Acta 34, 894–897 (1951)] to the compounds of formula I, wherein n=0. The preparation of the compounds of formula I, wherein n is the number 1 or 2, is carried out, for example, by oxidation of the compounds of formula I, wherein n=0, with an aqueous hydrogen peroxide solution.

Component (b) is suitable for stabilising nonblack elastomers against oxidative, thermal, light- or ozone-induced degradation.

Elastomers are understood as meaning macromolecular materials which, after substantial deformation through minor stress, are capable of rapidly regaining their approximate original shape-at room temperature; see also Hans-Georg Elias, An Introduction to Polymer Science, chapter 12; Elastomers, pages 388–393, 1997, VCH Verlagsgesellschaft mbH, Weinheim, Germany; or Ullmann's Encyclopedia of Industrial Chemistry, Fifth, completely revised Edition, Volume A 23, pages 221–440 (1993).

The compositions of this invention may contain, for example, the following materials as elastomers:
1. Polymers of diolefins, such as polybutadiene or polyisoprene.
2. Copolymers of mono- and diolefins with each other or with other vinyl monomers, such as propylene/isobutylene copolymers, propylene/butadiene copolymers, isobutylene/isoprene copolymers, ethylene/alkylacrylate copolymers, ethylene/alkylmethacrylate copolymers, ethylene/vinyl acetate copolymers, acrylonitrile/butadiene copolymers and terpolymers of ethylene with propylene and a diene, such as hexadiene, dicyclopentadiene or ethylidenenorbornene.
3. Copolymers of styrene or a-methylstyrene with dienes or acryl derivatives, for example styrene/butadiene, styrene/butadiene/alkylacrylate and styrene/butadiene/ methacrylate; and also block copolymers of styrene, such as styrene/butadiene/styrene or styrene/isoprene/styrene.
4. Halogen-containing polymers, for example polychloroprene, chlorinated rubber, chlorinated and bromated copolymer of isobutylene/isoprene (halobutyl rubber).
5. Natural rubber.
6. Aqueous emulsions of natural or synthetic rubbers, such as natural rubber latex or latices of carboxylated styrene/butadiene copolymers.

The nonblack elastomer to be protected is preferably a nonblack vulcanised elastomer. Non-black (carbon black-free) polydiene vulcanisates or nonblack halogen-containing polydiene vulcanisates are particularly preferred, in particular nonblack (carbon black-free) styrene/butadiene copolymer vulcanisates.

Component (b) is conveniently added to the elastomer to be stabilised in an amount of 0.2 to 10%, for example of 0.5 to 5%, preferably of 0.8 to 3.0%, based on the weight of the elatstomer to be stabilised.

In addition to components (a) and (b), the novel compositions can also contain further additives, such as the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl4-methylphenol, 2-(α-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4dioctylthiomethyl-6-tert-butylphenol, 2,4-dioctythiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-tert-butylhydroquinone, 2,5di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl4-hydroxyphenyl stearate, bis(3,5-di-tert-butyl-4-hydroxyphenyl) adipate. 1.4. Tocopherols, for example α-tocopherol, β-tocopherol, γ-tocopherol, δ-tocopherol and mixtures thereof (Vitamin E). 1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide. 1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-dimethylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)-malonate, di-octadecyl-2-(3-tert-butyl4-hydroxy-5-methylbenzyl)-malonate, didodecylmercaptoethyl-2,2-bis(3,5-di-tert-butyl-4-hydroxybenzyl)malonate, bis[4-(1,1,3,3-te-tramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxy-benzyl)-2,4,6-trimethylbenzene, 1,4-bis(3,5-di-tert-butyl-4-hydroxybenzyl)-2,3,5,6-tetrame-thylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenylcarbamate.

1.13. Esters of β-(3.5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trime-thylolpropane, 4-hydroxymethyl-1-phospha-2,6,7-trioxabicyclo[2.2.2] octane.

1.15. Esters of β-(3,5-dicyclohexyl-4-hydroxyphenyl) propionic acid with mono- or polyhydric alcohol, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octa-decanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl4,4'-diaminodiphenylmethane, 1,2-bis[(2-methylphenyl)amino]ethane, 1,2-bis(phenylamino)-propane, (o-tolyl)biguanide, bis[4(1',3'-dimethylbutyl) phenyl]amine, tert-octylated N-phenyl-1-naphthylamine, a mixture of mono- and dialkylated tert-butyl-tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, octylphenothiazine, a mixture of mono- and dialkylated tert-butyl-tert-octylphenothiazines, a mixture of mono- und dialkylated tert-octyl-phenothiazines, N-allyl-phenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'bis(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3-tert-butyl-5-[2-(2-ethylhexyloxy) carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl) phenyl]-benzotriazole; 2[2'-hydroxy-3'-(1,1,3,3tetramethylbutyl)5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4dimethylphenyl)-1,3,5-triazine, 2-(2,4-dihydroxyphenyl)4,6-bis(2,4dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/ridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(dimethylphenyl)-1,3,5-triazine.

3. Metal deactivators, for example N,N'-diphenyloxamde, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butyl-phenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocin, 6-fluoro-2,4,8,10tetra-tert-butyl-12-methyl-dibenz[d,g]-1,3,2-dioxaphosphocin, bis(2,4di-tert-butyl-6-methylphenyl)methyl phosphite, bis(2,4di-tert-butyl-6-methylphenyl)ethyl phosphite, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

5. Hydroxylamines, for example N,N-dibenzylhydroxylamine, N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, Noctadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

10. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

11. Fillers and reinforcing agents, for example carbon black, calcium carbonate, silicates, glass fibres, glass beads, talcum, kaolin, mica, barium sulfate, metal oxides and metal hydroxides, graphite, wood flour and flours or fibers of other natural products, synthetic fibers .

12. Other additives, for example plasticisers, such as mineral oils or dioctylphthalate, lubricants, emulsifiers, pigments, such as titanium dioxide, rheology additives, catalysts, flow-control agents, dispersants, flameproofing agents, optical brighteners, antistatic agents, blowing agents, vulcanisation activators, such as zinc oxide or stearic acid, vulcanisation accelerators, such as mercaptobenzothiazole or dibenzothiazidedisulfide, vulcanising agents, such as sulfur or organic peroxides, charge control agents.

Preferred compositions of this invention additionally comprise as further additives one or more than one component selected from the group consisting of pigments, colourants, fillers, flow control agents, dispersants, plasticisers, vulcanisation activators, vulcanisation accelerators, vulcanising agents, charge control agents, adhesion promoters, light stabilisers or antioxidants, such as phenolic antioxidants, organic phosphites or phosphonites; and/or thiosynergists.

The additional additives are used, for example, in concentrations of 0.01 to 10%, based on the total weight of the nonblack elastomer to be stabilised.

Component (b) and optional further additives are incorporated into the nonblack elastomer by known methods, for example before or during moulding or vulcanisation or also by applying the dissolved or dispersed component (b) to the nonblack elastomer, if required with subsequent evaporation of the solvent. Component (b) and optional further additives can also be added to the nonblack elastomer to be stabilised in the form of a masterbatch comprising them e.g. in a concentration from 2.5 to 25% by weight Component (b) and optional further additives can also be added before or during the polymerisation of synthetic nonblack elastomers or before crosslinking.

Component (b) and optional further additives can be incorporated in the nonblack elastomer to be stabilised in pure form or encapsulated in waxes, oils or polymers.

Component (b) and optional further additives can also be applied by spraying to the non-black elastomer to be stabilised. They are capable of diluting other additives (e.g. the standard additives mentioned above) or their melts so that they can also be sprayed together with these additives to the nonblack elastomer to be stabilised. The addition by spray application during the deactivation of the polymerisation catalysts is particularly advantageous, it being possible to employ e.g. the steam used for deactivation for spraying.

The nonblack elastomers stabilised in this manner can be used in a very wide range of forms, e.g. as filaments, moulding compositions, profiles, conveyeor belts or tires.

This invention also relates to the novel compounds of formula I.

Accordingly, this invention also relates to compounds of formula I

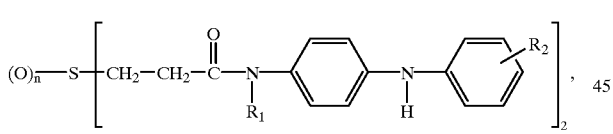

(I)

wherein

R$_1$ is hydrogen, C$_1$–C$_2$alkyl, cyclohexyl, phenyl or benzyl,

R$_2$ is hydrogen or C$_1$–$_4$alkyl, and n is the number 0, 1 or 2, with the proviso that the compound of formula (101)

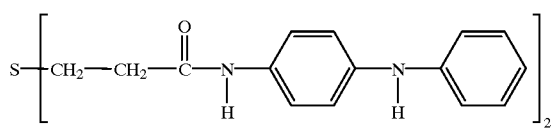

(101)

is excluded.

Preferred groups of novel compounds of formula I correspond to the preferred meanings given for the above novel compositions.

Particularly preferred are the novel compounds of formula I, wherein

R$_1$ is hydrogen or C$_3$–C$_8$alkyl,

R$_2$ is hydrogen, and n is the number 0 or 1, with the proviso that the compound of formula (101) is excluded.

The novel compounds of formula I can be reacted, for example, starting from the known compounds of formula II

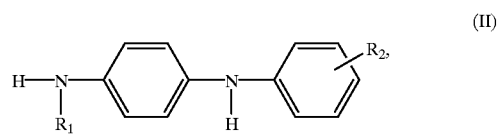

(II)

with half an equivalent of thio-3,3-bispropionic acid dichloride [preparation see H. Schmid et al., Helvetica Chimica Acta 34, 894–897 (1951)] to the compounds of formula I, wherein n=0. The preparation of the compounds of formula I, wherein n is the number 1 or 2, is carried out, for example, by oxidation of the compounds of formula I, wherein n=0, with an aqueous hydrogen peroxide solution.

In another of its aspects, this invention relates to a process for stabilising and reducing the discoloration of nonblack elastomers, which comprises incorporating in, or applying to, said elastomers at least one component (b).

A preferred embodiment of this invention is the use of component (b) as colour-stable and nonstaining stabilisers and antiozonants for protecting nonblack elastomers against oxidative, thermal, light- or ozone-induced degradation.

The invention is illustrated by the following Examples. Parts and percentages are by weight.

EXAMPLE 1

Preparation of thio-3,3-bispropionic Acid di(4-phenylamino)anilide [compound (101)]

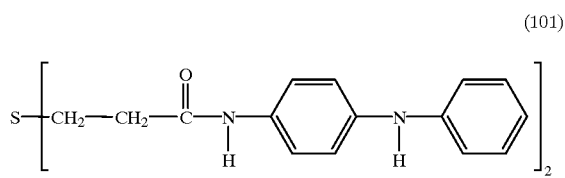

(101)

27.8 g (0.129 mol) of thio-3,3-bispropionic acid dichloride [preparation see H. Schmid et al., Helvetica Chimica Acta 34, 894–897 (1951)] are added dropwise over one hour to a solution, cooled to 0–5° C., of 43.29 g (0.235 mol) of 4-aminodiphenylamine and 25.3 g (0.351 mol) of pyridine in 240 ml of dimethylformamide. Subsequently, 120 ml of water are added and the precipitated product is filtered. The residue is washed with 3×120 ml of warm (80° C.) water and is then dried in a drying oven under water-jet vacuum at about 40° C. Crystallisation of the residue from dimethylformamide/toluene affords 44.8 g (74.5%) of a white powder, m.p. 216.5–217° C. [compound (101)]. Analysis calculated: C 70.56; H 5.92; N 10.97; S 6.28%. Analysis found: C 70.70; H 5.93; N 10.97; S 6.04%.

EXAMPLE 2

Preparation of thio-3,3-bispropionic Acid di(N-isopropyl-4-phenylamino)anilide [compound (102)]

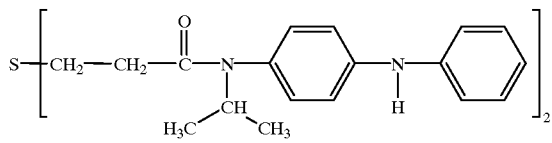
(102)

40 g (0.186 mol) of thio-3,3-bispropionic acid dichloride [preparation see H. Schmid et al., Helvetica Chimica Acta 34, 894–897 (1951)] are added dropwise over one hour to a solution, cooled to −20° C., of 70.1 g (0.31 mol) of 4-isopropylaminodiphenylamine [Vulkanox® 4010, Bayer] and 33.3 (0.465 mol) of pyridine in 370 ml of dimethylformamide. Subsequently, 800 ml of toluene and 800 ml of water are added and the mixture is heated to about 95° C. The hot organic phase is separated, washed with hot water, dried over sodium sulfate and concentrated in a vacuum rotary evaporator. The residue is crystallised from toluene and the crystals are dried in a high-vacuum drying oven at 125–130° C., affording 68.2 g (74%) of a white powder, m.p. 144.5–145.5° C. [compound (102)]. Analysis calculated: C 72.69; H 7.12; N 9.42; S 5.39%. Analysis found: C 72.59; H 7.07; N 9.48; S 5.39%;

EXAMPLE 3

Preparation of sulfinyl-3,3-bispropionic Acid di(N-isopropyl-4-phenylamino)anilide [compound (103)]

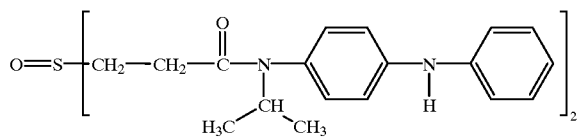
(103)

8.49 g (0.074 mol) of a 30% aqueous $H_2O_2$ solution are added to a solution of 22.3 g (0.037 mol) of compound (102) [Example 2] in 100 ml of acetone and 200 ml of methylenechloride at room temperature, and the reaction mixture is stirred for 64 hours at room temperature. The solvent is then concentrated in a vacuum rotary evaporator and the residue is dissolved in chloroform. The organic phase is washed with water, dried over sodium sulfate and concentrated in a vacuum rotary evaporator. The residue is crystallised from methylenechloride/acetone, affording 19.4 g (85%) of a white powder, m.p. 176.0–176.5° C. [compound (103)]. Analysis calculated: C 70.79; H 6.93; N 9.17; S 5.25%. Analysis found: C 69.98; H 6.93; N 9.12; S 4.96%.

EXAMPLE 4

Stabilisation of Nonblack SBR Vulcanisate 100 parts by weight of Cariflex®S-1502 (styrene/butadiene rubber, of Shell) are processed in a mixing mill at 60° C. to a homogeneous mixture with 30.0 parts by weight of Kronos®CL 220 [titanium dioxide (pigment), of Kronos Titan GmbH], 30.0 parts by weight of Aktisil®MM [kaolin (filler), of Hoffmann Mineral Neuburg/Donau], 5.0 parts by weight of Naftolen®N 401 [plasticiser, of Metallgesellschaft], 10.0 parts by weight of zinc oxide [vulcanisation activator], 2.0 parts by weight of stearic acid [vulcanisation activator], 2.0 parts by weight of sulfur [vulcanising agent], 1.0 parts by weight of Vulkacit®MOZ [vulcanisation accelerator, of Bayer], 0.25 part by weight of Vulkacit®Thiuram [vulcanisation accelerator, of Bayer] and 2.0 parts by weight of the stabiliser to be tested of Table 1, the vulcanisation system (sulfur, Vulkacit®-MOZ and Vulkacit®Thiuram) being added only at the end of the mixing process. The mixture is vulcanised at 150° C. in electrical hot presses to T95 of the rheometer curves to elastomer plates 2 mm thick, 21 cm long and 8.0 cm wide.

The action of ozone is tested on one part of the elastomer plates so obtained according to standard ASTM D 3395–86 at dynamic elongation. To this purpose, the plates are first stored for 30 days in a standard operating environment [23/50 SN-ISO 291]. Subsequently, 20 cm×1 cm test samples are punched out and subjected to an ozone atmosphere for 96 hours (ozone content: 50 pphm; temperature: 40° C.; humidity: 50% rel.; elongation: 0 to 25%; rate of elongation: 0.5 Hz; number of load alternation: about 173, 000). The test plates are then assessed for cracking according to ASTM D 3395–86. Grade 0 denotes no cracks; grade 1 denotes narrow, shallow cracks; grade 2 denotes moderately wide, moderately deep cracks, clearly visible; grade 3 denotes wide and deep cracks. The lower the grade number, the better the stabilisation of the elastomer plates. The results are compiled in Table 1.

The other part of the elastomer plates is stored for 10 weeks at room temperature in a normal laboratory atmosphere in diffuse daylight. The ΔL-colour of these plates is then determined in accordance with DIN 6167, corresponding to a scale from 0 to 100. No discoloration means a value of 100. The results are compiled in Table 1.

TABLE 1

| Examples | Stabiliser | Cracking according to ASTM D 3395-86 | ΔL-Colour according to DIN 6167 |
|---|---|---|---|
| Example 4a[a] | — | Grade 1–2 | 96 |
| Example 4b[a] | 2.0 phr[c] Vulkanox ® 4010[d] | Grade 0 | 37 |
| Example 4c[b] | 2.0 phr[c] compound (101) | Grade 1 | 94 |
| Example 4d[b] | 2.0 phr[c] compound (103) | Grade 0–1 | 75 |

[a]Comparison Examples.
[b]Examples of this invention.
[c]phr means parts per hundred of rubber
[d]Vulkanox ® 4010 (Bayer) means 4-isopropylaminodiphenylamine of formula A

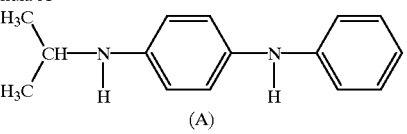
(A)

What is claimed is:

1. A compound of formula I

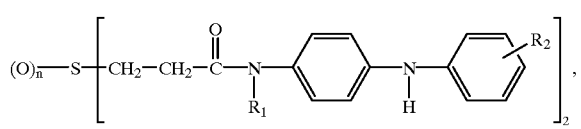

wherein
R₁ C₃–C₈alkyl,
R₂ is hydrogen or C₁–C₄alkyl, and
n is the number 1 or 2.

2. A compound according to claim 1, wherein
R₁ is hydrogen or C₃–C₈alkyl,
R₂ is hydrogen, and
n is the number 0 or 1.

3. A composition, which comprises
a) a carbon black-free elastomer subject to oxidative, thermal, light- or ozone-induced degradation, and
b) at least one compound of formula I

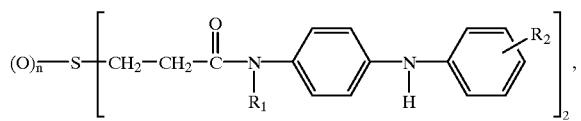

wherein
R₁ is C₃–C₈alkyl,
R₂ is hydrogen or C₁–C₄alkyl, and
n is the number 1 or 2.

4. A composition according to claim 3, wherein component (b) is at least one compound of formula I, wherein
R₁ is C₃–C₈alkyl,
R₂ is hydrogen or methyl, and
n is the number 1.

5. A composition according to claim 3, wherein component (b) is at least one compound of formula I, wherein
R₁ is C₃–C₈alkyl,
R₂ is hydrogen, and
n is the number 1.

6. A composition according to claim 3, wherein component (a) is a nonblack polydiene vulcanisate or a nonblack halogen-containing polydiene vulcanisate.

7. A composition according to claim 3, wherein component (a) is a nonblack styrene/butadiene copolymer vulcanisate.

8. A composition according to claim 3, which comprises additional additives besides components (a) and (b).

9. A composition according to claim 8, wherein the additional additives are one or more than one component from the group consisting of pigments, colourants, fillers, flow control agents, dispersants, plasticisers, vulcanisation activators, vulcanisation accelerators, vulcanising agents, charge control agents, adhesion promoters, antioxidants and light stabilisers.

10. A composition according to claim 8, wherein the additional additives are phenolic antioxidants, organic phosphites or phosphonites; and/or thiosynergists.

11. A composition according to claim 3, wherein component (b) is present in an amount of 0.2 to 10%, based on the weight of component (a).

12. A process for stabilizing and reducing the discoloration of carbon black-free elastomers, which comprises incorporating in, or applying to, said elastomers at least one compound of formula I

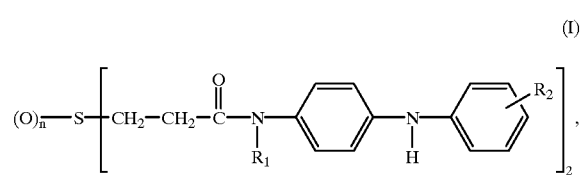

wherein
R₁ is C₃–C₈alkyl,
R₂ is hydrogen or C₁–C₄alkyl, and
n is the number 1 or 2.

* * * * *